(12) United States Patent
McCormick et al.

(10) Patent No.: US 10,471,229 B2
(45) Date of Patent: Nov. 12, 2019

(54) RESPIRATORY SUPPORT SYSTEM AND PATIENT TRANSFER DEVICE THEREFOR

(71) Applicant: General Electric Company, Schenectady, NY (US)

(72) Inventors: Timothy Patrick McCormick, Madison, WI (US); Bradley Baum, Madison, WI (US); Andreas Tzanetakis, Madison, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1128 days.

(21) Appl. No.: 14/470,405

(22) Filed: Aug. 27, 2014

(65) Prior Publication Data
US 2016/0058967 A1 Mar. 3, 2016

(51) Int. Cl.
*A61M 16/08* (2006.01)
*A61M 16/00* (2006.01)
*A61M 16/20* (2006.01)

(52) U.S. Cl.
CPC .... *A61M 16/0883* (2014.02); *A61M 16/0045* (2013.01); *A61M 16/0816* (2013.01); *A61M 16/204* (2014.02); *A61M 16/205* (2014.02); *A61M 16/0075* (2013.01); *A61M 16/0081* (2014.02); *A61M 2016/0027* (2013.01); *A61M 2205/128* (2013.01); *A61M 2205/35* (2013.01); *A61M 2205/502* (2013.01); *A61M 2205/52* (2013.01); *A61M 2205/6009* (2013.01); *A61M 2205/6018* (2013.01);
(Continued)

(58) Field of Classification Search
CPC .......... A61M 16/0883; A61M 16/0816; A61M 16/0045; A61M 2209/086

USPC .......... 128/204.21, 204.22, 202.27
See application file for complete search history.

(56) References Cited

U.S. PATENT DOCUMENTS 1,005,816 A * 10/1911 Drager ............... A61M 16/08
128/202.27
3,038,472 A * 6/1962 Gaylord ............... B64D 25/00
128/202.27
(Continued)

OTHER PUBLICATIONS

Drager Evita Infinity V500 Brochure, by Drager Medical GmbH, Sep. 2010.

*Primary Examiner* — Tan-Uyen T Ho
*Assistant Examiner* — Victoria Murphy
(74) *Attorney, Agent, or Firm* — Andrus Intellectual Property Law, LLP

(57) ABSTRACT

A patient transfer device is configured for use with at least one host device which is capable of providing respiratory support to a patient. The patient transfer device includes an inspiratory port and an expiratory port which are configured to pneumatically connect to the host. An inspiratory connection is pneumatically connected to the inspiratory port and an expiratory connection is pneumatically connected to the expiratory port. An inspiratory valve is coupled between the inspiratory port and the inspiratory connection and expiratory valve is coupled between the expiratory port and the expiratory connection. The inspiratory valve and the expiratory valve are operable between first configurations that permit flow there though and second configurations that occlude flow through the valves. The inspiratory valve and the expiratory valve are configured to operate in the second configuration when the patient transfer device is disconnected from the at least one host device.

17 Claims, 5 Drawing Sheets

(52) U.S. Cl.
CPC .............. *A61M 2205/6054* (2013.01); *A61M 2205/8206* (2013.01); *A61M 2230/205* (2013.01); *A61M 2230/30* (2013.01); *A61M 2230/43* (2013.01)

(56) References Cited

U.S. PATENT DOCUMENTS

| | | | | | |
|---|---|---|---|---|---|
| 3,166,676 | A | * | 1/1965 | Robinson | A61M 16/104 128/204.14 |
| 3,185,148 | A | * | 5/1965 | Gaylord | B64D 25/00 128/202.13 |
| 3,200,816 | A | * | 8/1965 | Bartlett, Jr. | A61M 16/00 128/204.21 |
| 5,319,363 | A | * | 6/1994 | Welch | H04Q 9/00 340/12.3 |
| 5,497,766 | A | * | 3/1996 | Foster | A61G 7/00 128/200.24 |
| 5,701,883 | A | * | 12/1997 | Hete | A61M 16/12 128/204.21 |
| 6,158,430 | A | * | 12/2000 | Pfeiffer | A61M 16/00 128/202.27 |
| 6,571,792 | B1 | * | 6/2003 | Hendrickson | A61M 16/08 128/202.22 |
| 8,118,024 | B2 | * | 2/2012 | DeVries | A61M 16/0057 128/204.21 |
| 8,156,937 | B2 | * | 4/2012 | DeVries | A61M 16/026 128/200.24 |
| 8,225,788 | B2 | * | 7/2012 | Manigel | A61M 16/01 128/200.24 |
| 8,627,819 | B2 | * | 1/2014 | DeVries | A61M 16/0057 128/200.24 |
| 8,770,191 | B2 | * | 7/2014 | Tham | A61M 16/024 128/204.21 |
| 2003/0183232 | A1 | * | 10/2003 | Fukunaga | A61M 16/0045 128/204.18 |
| 2005/0188990 | A1 | * | 9/2005 | Fukunaga | A61M 16/08 128/204.18 |
| 2012/0174925 | A1 | * | 7/2012 | Tham | A61M 16/0051 128/204.21 |
| 2016/0058967 | A1 | * | 3/2016 | McCormick | A61M 16/0883 128/204.21 |

* cited by examiner

RESPIRATORY SUPPORT SYSTEM AND PATIENT TRANSFER DEVICE THEREFOR

BACKGROUND

The present disclosure is related to the field of mechanical ventilation. More specifically, the present disclosure is related to a patient transfer device and ventilation system to facilitate transfer of a patient between respiratory support devices.

In the course of a medical treatment, a patient may require some form of respiratory support, which is provided by a ventilator. Respiratory support may include assisted breathing, wherein the ventilator detects breath attempts and provides supplemental pressure and gas flow for the patient to complete and effective respiratory cycle. More severely conditioned patients may require mechanical ventilation, whereby the ventilator also initiates the respiratory phase of each respiratory cycle. During, the course of treatment, the patient receiving respiratory support may require to be transferred between ventilator systems. One example of this transfer may occur when a patient is switched between receiving respiratory support from an anesthesia ventilator as may be used when surgery is performed on the patient and an intensive care unit (ICU) ventilator to which the patient may be connected before and/or after the surgical procedure. This transfer necessarily requires the disconnection of the patient from one ventilator before connection to another, leaving a time period when the patient is disconnected from receiving respiratory support from either ventilator.

Previous solutions have used a basic ventilator unit which remains connected to the patient and is transferred between respiratory systems. However, this solution requires transport of the ventilator unit itself which is cumbersome and presents an additional challenge for movement of a critical care patient. Furthermore, as such a ventilator unit is intended to be moved with the patient, the ventilator unit is of basic or limited functionality when a critical care patient may require the benefits of more complex systems.

BRIEF DISCLOSURE

An exemplary embodiment of a patient transfer device is used with at least one host device which is capable of providing respiratory support to a patient. The patient transfer device includes an inspiratory port configured to pneumatically connect to the at least one host device to receive a flow of inspiratory gases. An inspiratory connection is pneumatically connected to the inspiratory port. An inspiratory valve is coupled between the inspiratory port and the inspiratory connection. The inspiratory valve is operable between a first configuration that permits flow between the inspiratory port and the inspiratory connection and a second configuration that occludes flow between inspiratory port and inspiratory connection. An expiratory port is configured to pneumatically connect to the at least one host device. An expiratory connection is pneumatically connected to the expiratory port. An expiratory valve is coupled between the expiratory port and expiratory connection. The expiratory valve is operable between a first configuration that permits flow between the expiratory port and expiratory connection and a second configuration that occludes flow between the expiratory port and expiratory connection. The inspiratory valve and the expiratory valve are configured to operate in the second configuration when the patient transfer device is disconnected from at least one host device.

An exemplary embodiment of a respiratory support system includes a first host device which includes a first ventilator and first transfer bay. The first host device is configured to provide respiratory support to a patient. A second host device includes a second ventilator and a second transfer bay. The second host device is configured to provide respiratory support to the patient. The patient transfer module is configured to be received within either of the first transfer bay and the second transfer bay. The patient transfer device includes an inspiratory port configured to selectively pneumatically connect to the first or second host devices to receive flow of inspiratory gases from the first and second ventilator. An inspiratory connection is pneumatically connected to the inspiratory port. An expiratory port is configured to pneumatically connect to the at least one host device. An expiratory connection is pneumatically connected to the expiratory port. An inspiratory valve is coupled between the inspiratory port and inspiratory connection. The inspiratory valve is operable between a first configuration that permits flow between an inspiratory port and the inspiratory connection and a second configuration that occludes flow between the inspiratory port and inspiratory connection. An expiratory valve is coupled between the expiratory port and the expiratory connection. The expiratory valve is operable between a first configuration that permits flow between the expiratory port and the expiratory connection and a second configuration that occludes flow between the expiratory port and the expiratory connection. The inspiratory valve and expiratory valve are configured to operate in the second configuration when the patient transfer device is disconnected from the first and second host devices. A breathing circuit includes a patient interface configured to pneumatically seal across an airway of the patient. An inspiratory limb is coupled between the inspiratory connection and the patient interface. An expiratory limb is coupled between the expiratory connection and the patient interface.

An exemplary embodiment of a method of providing respiratory support to a patient includes delivering respiratory support to the patient with a first host device which includes a ventilator through a transfer device which receives a flow of inspiratory gases from the first host device through an inspiratory port and provides inspiratory gases to the patient through a breathing circuit. Expired gases from the patient are returned through the breathing circuit and an expiratory port of the transfer device to the first host device. An inspiratory valve associated with the inspiratory port is closed and an expiratory valve associated with the expiratory port is closed to create a closed pneumatic system between the breathing circuit and the transfer device. The transfer device is disconnected from the first host device. The transfer device is reconnected to a second host device which includes a second ventilator. The inspiratory valve and the expiratory valve are opened. Respiratory support is delivered to the patient with the second host device through the transfer device which receives a flow of inspiratory gases from the second host device through the inspiratory port and provides the inspiratory gases to the patient through the breathing circuit. Expired gases from the patient are returned through the breathing circuit and the expiratory port of the transfer device to the second host device through the expiratory port.

DETAILED DISCLOSURE

Figure 1:
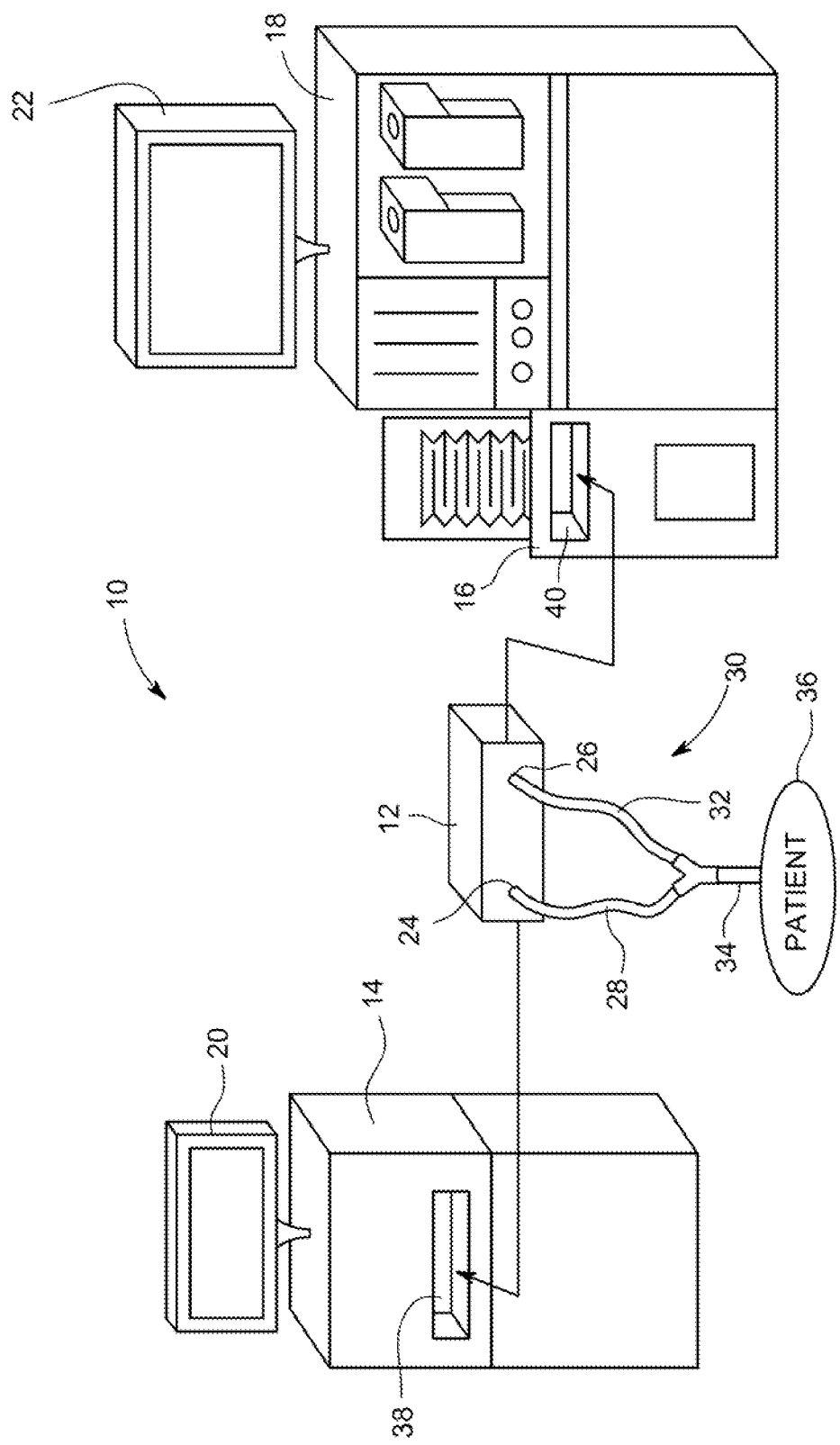
FIG. 1 is a system diagram of an exemplary embodiment of a respiratory support system.

FIG. 1 is a system diagram of an exemplary embodiment of a respiratory support system 10. The respiratory support system 10 includes a patient transfer device 12 and at least one host device. In the respiratory support system 10 depicted in FIG. 1 two exemplary host devices are depicted, which are exemplarily embodied by a ventilator 14 which may exemplary be found in an intensive care unit (ICU) and an anesthesia ventilator 16 which is connected to an anesthesia delivery unit 18 and may exemplarily be used in an operating room. As will be described in further detail herein, both host devices exemplarily include respective graphical displays 20, 22. The host device may further operate the graphical displays to comprise a user interface presented on the graphical displays 20, 22, although it will be recognized that the host devices 14, 18 may further include other forms of user input devices as will be recognized by a person of ordinary skill, although not depicted in FIG. 1.

The patient transfer device 12 further includes an inspiratory connection 24 and an expiratory connection 26. The inspiratory connection 24 is connected to an inspiratory limb 28 of a breathing circuit 30 and the expiratory connection 26 is connected to an expiratory limb 32 of the breathing circuit 30. The inspiratory limb 28 and expiratory limb 32 connect at a patient connection 34 which is configured to automatically connect to a patient 36.

In embodiments, the patient connection 34 is exemplarily an endotracheal (ET) tube or another patient connection suitable for the delivery of respiratory support. In embodiments, the patient connection is one that creates a pneumatic seal with the airway of the patient. Such a pneumatic seal enables the control and delivery of flows of medical gas and prescribed pressures into the respiratory system of the patient. As will be described in further detail herein, various pressures within the patient's airway, including, but not limited to inspiratory pressure and expiratory pressure may be controlled during respiratory support. A flow of medical gas is provided through the inspiratory limb 28 to the patient 36 through the patient connection 34 in an inspiratory phase and expired gases are directed from the patient 36 through the patient connection 34 to the expiratory limb 32 in an expiratory phase.

The at least one host device 14, 16 includes a transfer bay 38 configured to not only receive the patient transfer device 12 but also to facilitate the operable connection of the patient transfer device 12 to the respective host devices 14, 16. As will be described in further detail herein, the patient transfer device 12 is configured to and operable to connect to either of the transfer bays 38, 40 in a manner that exemplarily connect the devices for gas flow, power supply, and/or data communication.

The inventors have identified that a particular challenge exists when a patient receiving respiratory support must be transferred between ventilators especially when the patient is receiving, lung volume recruitment therapy. Certain medical conditions, includes, but not limited to atelectasis result in collapsed alveoli which are the air sacs within the lung wherein gas exchange with the patient's blood occurs. Collapsed alveoli can create a significant loss of lung, volume and impair the efficiency of gas exchange. Typically, the gas exchange removes carbon dioxide from the patient's blood while introducing oxygen to the patient's blood. Specialized forms of respiratory support known as recruitment procedures have been developed to progressively open up or "recruit" collapsed alveoli. Recruitment procedures may use specialized medical gases such as helium in addition to other medical gases of oxygen, nitrogen and air or other additives such as surfactant in order to reduce airway resistance. Still, recruitment procedures typically involve a series of prescribed ventilation pressure, including, but not limited to inspiratory pressure and expiratory pressure. Positive end expiratory pressure (PEEP) is a common component of a prescribed recruitment procedure. PEEP puts a positive pressure on the patient's airway at the end of an expiratory phase of a breathing cycle to "hold open" open alveoli which would normally collapse under ambient pressure. Thus, the PEEP therapy preserves recruited lung volume, maintaining the lung volume gains achieved through the recruitment procedure.

Recruitment procedures typically occur over a period of time which may be hours or days. The recruitment procedure must take place over a time period as patients in need of lung, recruitment typically also have low lung compliance and the recruited volume is desired to be gained from opening of alveoli rather than lung distension. Therefore, the recruitment procedure slowly increases the pressure applied to the lung over time as more alveoli are recruited and lung volume is gained. However, as noted above, typically when a patient is transferred between ventilators at some point in the transition the patient must be disconnected from one ventilator and reconnected to the other ventilator. Even if this transition period is a short period of time (e.g. less than one minute) the loss of the PEEP maintained in the system can cause the recruited alveoli to collapse, giving up any physiological gains that have been made through the previous recruitment procedure and other respiratory support. A new recruitment procedure or procedures must be performed over the aforementioned hours or days in order to re-recruit the lost lung volume. Therefore, embodiments of the patient transfer device 12 as disclosed in further detail herein preserves the numeric conditions of the patient such that recruited lung volume is maintained when ventilation resumes with the second ventilator.

Figure 2:
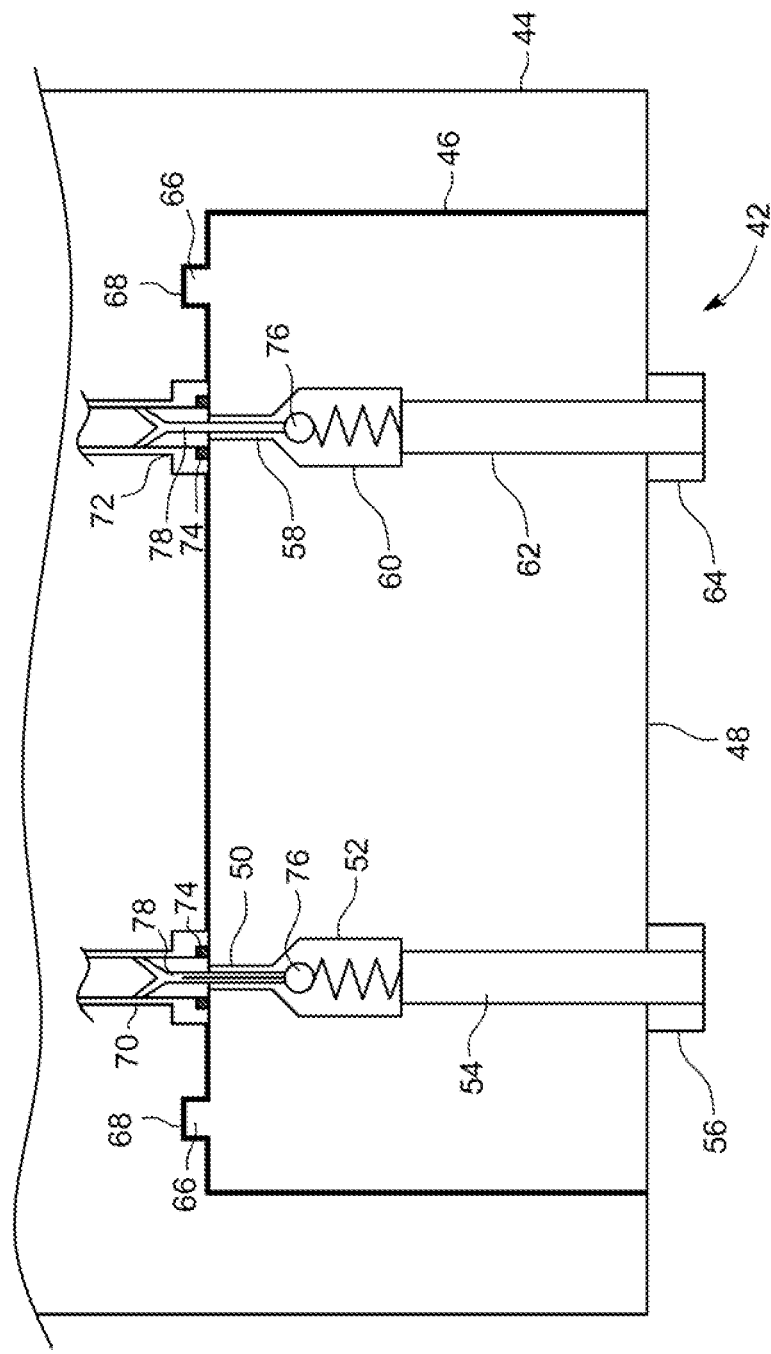
FIG. 2 is a partial cross sectional view of an exemplary embodiment of a patient transfer device connected to a host device.
Figure 3:
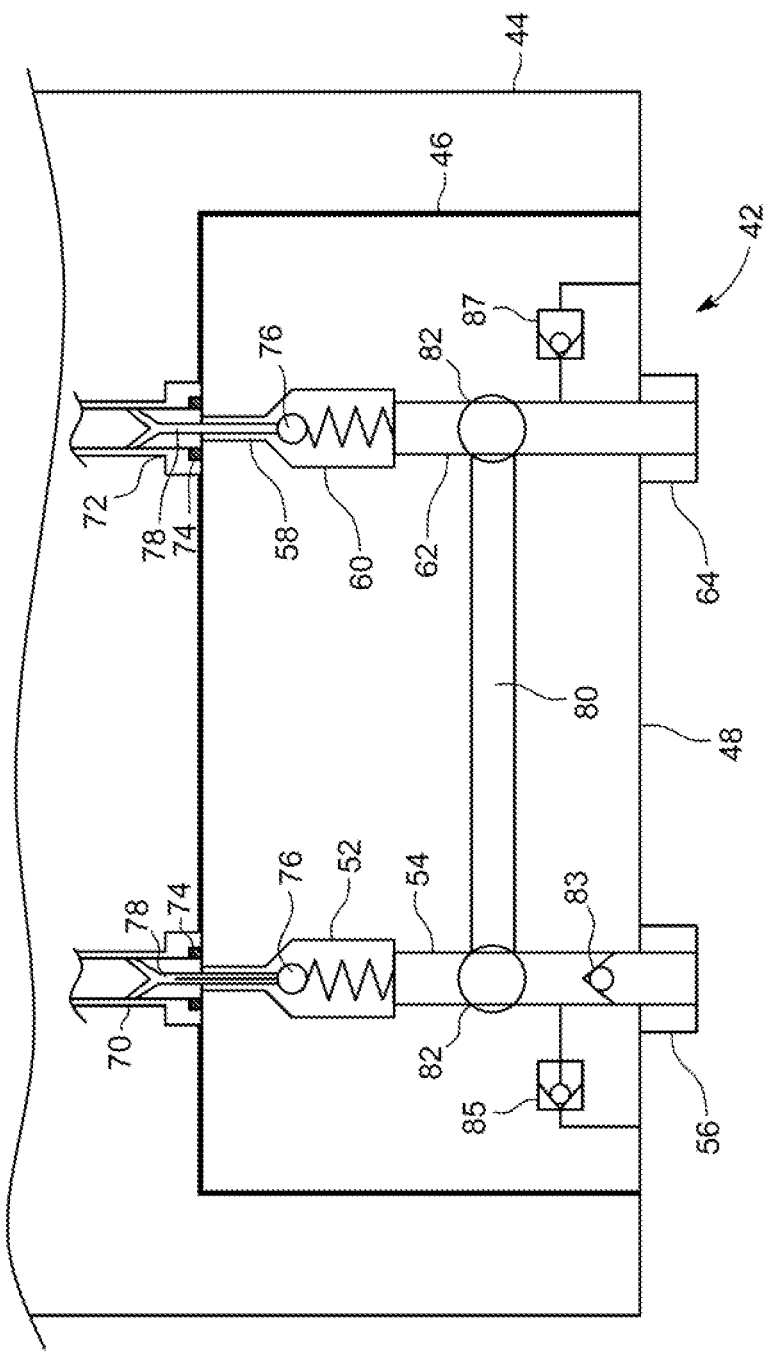
FIG. 3 is a partial cross sectional view of an additional exemplary embodiment of a patient transfer device connected to a host device.
Figure 4:
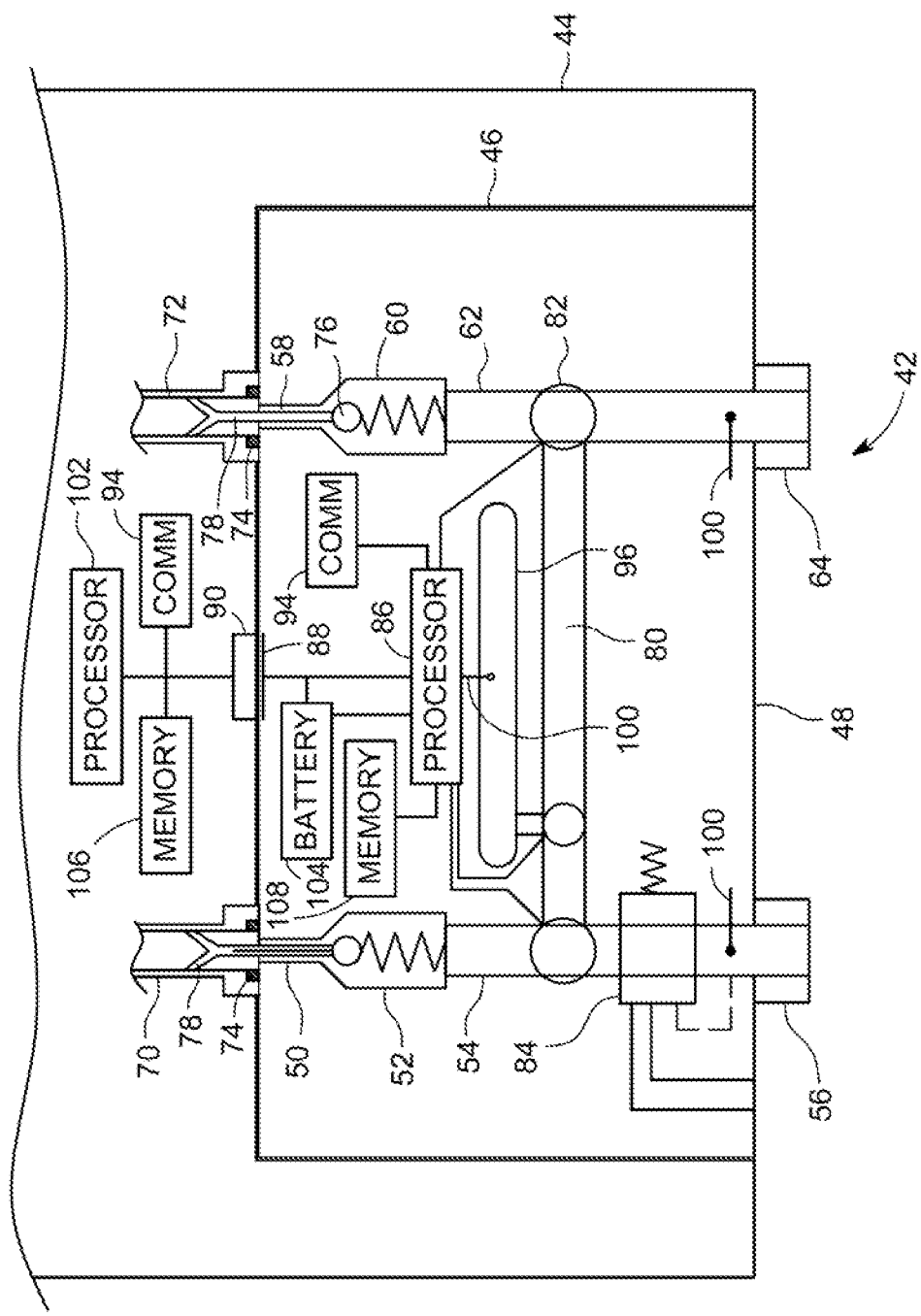
FIG. 4 is a partial cross section view of a still further exemplary embodiment of a patient transfer device connected to a host device.

FIGS. 2-4 depict partial cross sectional views of various exemplary embodiments of respiratory support systems, including patient transfer devices. It will be recognized that these exemplary embodiments are arranged for descriptive purposes and that still further embodiments including various combinations of features as disclosed in respective embodiments, as well as including other features as may be recognized by a person of ordinary skill in the art are within the scope of embodiments presently disclosed. Similar reference numerals are used across embodiments in order to facilitate conciseness and clarity of disclosure.

Specifically referring to FIG. 2, a cross sectional view of an exemplary embodiment of a respiratory support system 42 is depicted. The respiratory support system 42 includes a host device 44 which includes a transfer bay 46 within which a patient transfer device 48 is disposed. As noted above, the respiratory support system 42 includes at least one host device 44, which is exemplarily a ventilator and/or a ventilator associated with or comprising an anesthesia delivery unit. In an alternative exemplary use of embodiments as disclosed herein, the patient transfer device 48 may facilitate a temporary disconnection of the patient from the host device 44 exemplarily for service, maintenance, or cleaning of the host device 44 before the patient transfer device 48 is returned to the transfer bay 46 of the host device 44.

The patient transfer device 48 exemplarily includes an inspiratory port 50 which is configured to fluidly and adequately connect to the host device 44 as described in further detail herein in such a manner as to receive the flow of inspiratory gases, which may be delivered by the host device in accordance to a one-way pertinent procedure. An inspiratory valve 52 is connected to the inspiratory port 50. The inspiratory valve 52 is passively or actively operated to open to fluid flow when the transfer device 48 is connected to the host device 44 and then to close to fluid flow when the patient transfer device 48 is disconnected from the host device 44. An inspiratory tube 54 connects the inspiratory valve 52 to an inspiratory connection 56 that extends from the patient transfer device 48 and connects to an inspiratory limb at a breathing circuit (not depicted). Similarly, an expiratory port 58 is configured to removably connect to the host device 44 to facilitate transfer of expired gases through the patient transfer device 48 into the host device 44. Once directed into the host device 44, the expired gases may be processed for recirculation to the patient or vented outside of the host device 44. An expiratory valve 60 is further connected to the expiratory port 58. The expiratory valve 60 can be actively or passively operated to emit fluid flow through the expiratory valve 60 when the patient transfer device 48 is connected to the host device 44 and to be sealed off from fluid flow when the patient transfer device 48 is disconnected from the host device 44. An expiratory tube 62 extends from the expiratory valve 60 to an expiratory connection 64. The expiratory connection 64 is configured to connect to an expiratory limb of a breathing circuit (not depicted). The expiratory connection 64 received expired gases front the patient via the expiratory limb of the breathing circuit and, when the expiratory valve 60 is open, directed the expired gases out of the patient transfer device 48 and into the host device 44.

Exemplary embodiments of the patient transfer device 48 further include at least one registration feature 66 which is exemplary a keyed or other shaped feature that registers with and engages a corresponding registration feature 68 found in the transfer bay 46 of the host device 44. These one or more registration features can further help to ensure desired alignment and connection between the patient transfer device 48 and the host device 44. The host device 44 further includes an inspiratory outlet 70 and an expiratory inlet 72. The inspiratory outlet is configured to sealingly engage the inspiratory port 50 of the patient transfer device 48 and the expiratory inlet 72 is configured to sealingly engage the expiratory port. 58 of the patient transfer device. Respective o-rings 74 or other elastomer seals or gaskets facilitate these fluid tight seals between the host device 44 and the patient transfer device 48.

In the exemplary embodiment depicted in FIG. 2, the inspiratory valve 52 and the expiratory valve 60 are ball valves which include a spring, biased valve stop 76 which is biased in the closed position to seat against an interior wall or a seat within the respective valve, closing the valve to fluid flow. Restrictive engagement pins 78 extending from the inspiratory outlet 70 and expiratory inlet 72 engage ball stops 76 when the patient transfer device 48 is connected to the host device 44, thus mechanically overcoming the biasing force on the ball stop 76 and opening the inspiratory valve 52 and expiratory valve 60 to fluid flow.

In operation and use, the patient transfer device 48 serves to close both the inspiratory limb and expiratory limb of a breathing circuit to fluid flow when the patient transfer device 48 is disconnected from the host device 44. Therefore, so long as the fluid seal at the patient connection is maintained, pressure within the patient's airway may be maintained while the patient transfer device is disconnected from a first host device and reconnected to a new host device.

FIG. 3 depicts an additional exemplary embodiment of a patient transfer device 48 and a host device 44 and a partial cut away view. In this additional exemplary embodiment, a recirculation tube 80 extends between the inspiratory tube 54 and the expiratory tube 62. At least one valve 82 is connected to the recirculation tube 80. FIG. 3 depicts an exemplary embodiment wherein two valves 82 are used, one valve 82 at the intersection of the inspiratory tube 54 and the recirculation tube 80 and another valve 82 at the intersection of the expiratory tube 62 and the recirculation tube 80. Alternatively, it will be recognized that one or more valves disposed within, and therefore pneumatically connected to, the recirculation tube 80 may serve similar functions and purposes as disclosed herein. In operation, the valves 82 are operated such that valves 82 close off the recirculation tube 80 when the patient transfer device 48 is connected to the hose device 44. When the patient transfer device 48 is disconnected from the host device 44, the valves 82 open the recirculation tube 80 to fluid flow, thus connecting the expiratory tube 62 to the inspiratory tube 54. In embodiments, this provides a limited recirculation of expired gases to a spontaneously breathing patient while the patient is disconnected from any ventilator as the patient transfer device 48 is switched between host devices, in some embodiments, it may be desirable to recirculate expired breathing gases on a limited basis, rather than closing the breathing circuit to gas flow all together. While trot depicted, in additional embodiments, gas treatment devices may be placed in line with the recirculation tube 80. Exemplary embodiments of these gas treatment devices may include a carbon dioxide absorber or a condensate sump, although these are merely exemplary and not intended to be limiting on the scope of gas treatment devices which may be used.

In a still further exemplary embodiment, check valves 83 are disposed within the inspiratory tube 54 and the expiratory tube 62. The check values 83 further ensure that any breathing gases which circulate within the transfer device 48, are maintained with in a direction such that flow of gases in the inspiratory tube 54 is directed towards the patient and flow of gas in the expiratory tube 62 is directed away from the patient. In a still further exemplary embodiment that includes the check valve 83, a free breathing valve 85 connected to the inspiratory tube 54. The free breathing valve 85 may be operated such that a spontaneously breathing patient being, transferred with the use of the transfer device 48 may spontaneous breath by drawing air into the patient transfer device 48 through the free breathing valve 85 at spontaneous inhalations. An exhalation valve 87 similarly disposed in connection to the expiratory tube 62 can be user settable at the air way pressure (e.g. PEEP) and exhaust the patients spontaneous exhalation. Such an exemplary embodiment may operate to maintain PEEP, yet facilitate spontaneous breathing by the patient while minimizing rebreathing of expired gas.

FIG. 4 depicts a still further exemplary embodiment of a respiratory support system 42 which includes a partial cut away view of a patient transfer device 48 and a host device 44. The exemplary embodiment of the patient transfer device 48 includes at least one pressure relief valve 84 disposed within any one or more of the inspiratory tube 54, expiratory tube 62, or recirculation tube 80. The pressure relief valve 84 may serve to open to mitigate an over pressure condition which may occur in the breathing circuit when the patient transfer device 48 is disconnected from the host device 44. An over pressure condition may occur for example if a patient coughs or something else occurs that significantly increase the pressure within the closed off breathing circuit. In a merely exemplary embodiment, the pressure relief valve 84 may open at a mechanically predetermined level such as, but not limited to, 30-40 cm $H_2O$, when a typical operating PEEP is often less than 10 cm $H_2O$.

In a still further exemplary embodiment, the patient transfer device 48 includes a processor 86. The processor 86 enables the patient transfer device 48 to actively operate the valves as found therein depending, upon a sensed condition between the patient transfer device 48 and the host device 44. In an exemplary embodiment, one or more electrical contacts 88 of the patient transfer device 48 electrically connect to one or more electrical contacts 90 of the host device 44 enabling the processor 86 to determine whether or not the patient transfer device 48 is connected to the host device 44. In additional exemplary embodiments, a wireless communication device 92 of the patient transfer device 48 serves a similar function by communicatively engaging a communication device 94 of the host device 44. Exemplary embodiments of the wireless communication devices 92, 94 may include RFID, near field communications, or inductive connections although these are not intended to be limiting. The electrical contacts 88, 90, and communication devices 92, 94 will also be described in further detail herein.

In still further embodiments, the valve 82 may be combined with the respective inspiratory valve 52 and expiratory valve 60 with implementation as a 3-way valve wherein in a first position of the combined valve gas flow from the inspiratory/expiratory ports is permitted to the inspiratory/expiratory tube while flow through the recirculation tube is blocked and in a second position, gas flow to the inspiratory port 50 and expiratory port 58 is blocked and gas flow from the expiratory tube 62 into the recirculation rube 80 and through the recirculation tube 80 into the inspiratory tube 54 is permitted.

In a still further exemplary embodiment as depicted in FIG. 4, embodiments of the patient transfer device 48 may include a pressure reservoir 96 which is selectively connected to the breathing circuit by a pressure valve 98. The pressure value 98 may exemplarily be located in the recirculation tube 80, although it will also be recognized that the pressure valve 98 may be located at the inspiratory tube 54 to the expiratory tube 62. Pressure transducer 100 may be exemplary located in the pressure reservoir 96 and one or both of the inspiratory tube 54 and expiratory tube 62. In exemplary embodiments, the pressure transducers 100 provide pressure signals to the processor 86 such that if the processor 86 detects that the pressure in the breathing circuit, when the patient transfer device 48 is disconnected from the host device 44, falls below the desired pressure level (e.g. PEEP) to be maintained by the patient transfer device 48 additional pressure stored in the pressure reservoir 96 is released into the breathing circuit by opening the pressure valve 98. Such a loss of pressure may exemplary occur due to small leaks in the breathing circuit or at the patient connection or exemplarily may occur after pressure is released by operation of the pressure relief valve 84. In embodiments, the processor 86 receives ventilator settings from the processor 102 of the host device 44 as will be described in further detail herein. In embodiments, the processor 86 may use this information to determine the pressure level within the breathing circuit by the patient transfer device 48 when the patient transfer device is disconnected from a host device. In other embodiments, the processor 86 may use the measurements from the pressure transducers 100 at the time of disconnection as the pressure to be maintained.

In an embodiment, when the patient transfer device 48 is connected to the host device 44 the processor 86 is communicatively connected either through electrical contacts 88, 90 or the communication devices 92, 94 to a processor 102 of the host device 44. The processor 102 and processor 86 may work in conjunction to maintain or re-pressurize the pressure reservoir 96 with gas through the inspiratory port 50 and inspiratory tube 54 through operation of the ventilator of the host device 44.

Some such embodiments of the patient transfer device 48 as disclosed herein ma further require a mobile power source, such as a battery to draw power from while the patient transfer device 48 is disconnected from a host device 44. In such embodiments, the battery 104 may similarly be charged by the host device 44 when the patient transfer device 48 is connected to the host device 44. The battery may be charged from power received across electrical contacts 88, 90 as communication devices 92, 94, or other such forms of charging, including inductive charging units. When the patient transfer device 48 is connected to the host device 44, the patient transfer device may operate using power received from the host device 48.

In operation and use, when the patient transfer device 48 is connected to the host device 44, the host device 44 includes the ventilator (not depicted) which operates to provide the respiratory support to the patient. Such ventilator is operated by the processor 102 according to a plurality of ventilator settings which may be stored in a host device 44 memory 106. The memory 106 may also record trend information regarding the respiratory support or any recruitment procedures that are presently being administered, or have been administered in the past to the patient. In still further embodiments, other physiological data may be acquired by the host device 48, including, but not limited to vital signs, respiration rate of a spontaneously breathing patient, expired gas composition, blood pressure, $SpO_2$, or other physiological information. In still further embodiment, patient data such as demographic information including age, height, weight, sex, or other patient data obtained from an electronic medical record may be stored at the memory 106 during the course of providing respiratory support to the patient. This patient specific information, including ventilator settings, ventilation history and/or patient data, may be transferred to the memory 108 of the patient transfer device 48 and stored thereon. By way of example, ventilator settings my include inspiratory pressure, expiratory pressure, inspiratory time, expiratory time, respiration rate (for a non-spontaneously breathing patient), medical gas composition or additives, and PEEP, although a person of ordinary skill will recognize other ventilator settings which may be used. Such ventilator settings may be input and/or controlled into the host device 48 through a user interface (not depicted) of the host device, in an exemplary embodiment, when the patient transfer device 48 is reconnected to a new host device, this patient specific information can be transferred to the new host device and respiratory support resumed at the previous ventilator settings, with clinician access to the patient data and ventilation history through the user interface and display of the new host device. This information access enables the clinician using the new host device to be more informed of the patient's overall condition.

Figure 5:
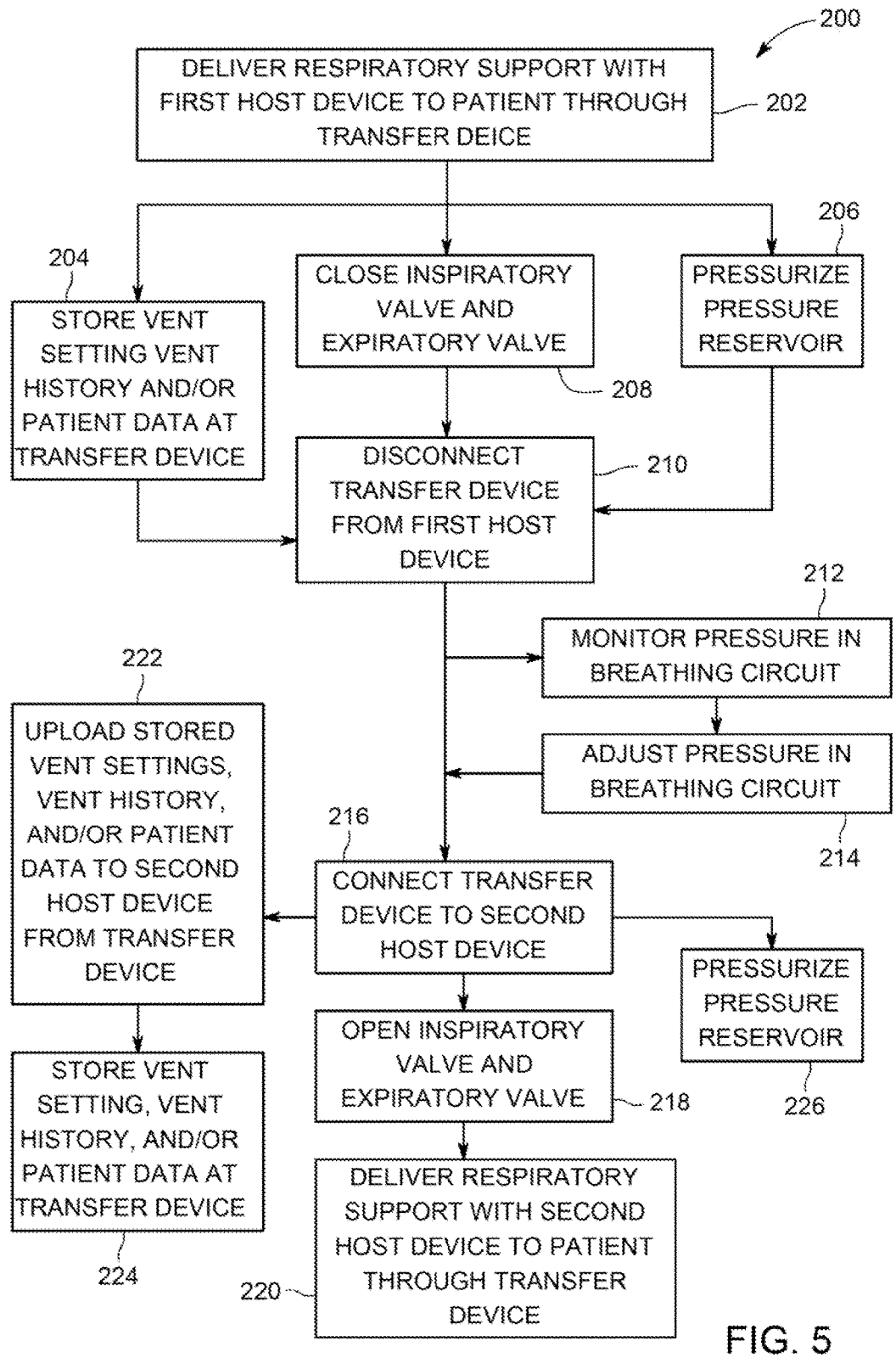
FIG. 5 is a flow chart that depicts an exemplary embodiment of a method of providing respiratory support to a patient.

FIG. 5 is a flow chart that depicts an exemplary embodiment of a method 200 of providing respiratory support to a patient. The method 200 begins at 202 with the delivery of respiratory support from a first host device to the patient though the transfer device. As explained above, during the delivery of respiratory support, the inspiratory gases and expired gases pass through the transfer device from the ventilator via the host device to the breathing circuit connected to the patient. In embodiments of the transfer device that include a memory, at 204 ventilator settings, ventilation history, and/or patient data is stored from the host device into the memory of the transfer device. In embodiments of the transfer device that include a pressure reservoir, at 206, the first host device and the transfer device work in conjunction to pressurize the pressure reservoir by diverting gas flow received at the inspiratory port of the transfer device into the pressure reservoir.

At 208, the inspiratory valve and expiratory valve of the transfer device are closed and at 210 the transfer device is disconnected from the first host device. In embodiments, the closing of the inspiratory valve and expiratory valve ma occur simultaneously with disconnection of the transfer device from the first host device. In alternative embodiments, the inspiratory valve and expiratory valve may be operated independently of the connection status between the transfer device and the host device and therefore may occur in the procedure before the transfer device is able to be removed. In an embodiment, the first host device provides respiratory support, which includes the maintenance of additional positive pressure on the airway of the patient. A specific example of this is known as positive end expiratory pressure (PEEP). By closing the inspiratory valve and expiratory valve prior to disconnection of the transfer device from the first host device, a closed pneumatic system is created and maintained between the transfer device and the breathing circuit to the patient airway. The transfer device operates to maintain this pressurized system as the transfer device is moved between the first host device and the second host device. In exemplary embodiments that include the pressure reservoir, at 212, the transfer device may monitor the pressure in the breathing circuit and if the monitored pressure in the breathing circuit drops below a predetermined threshold, which may be relative to the pressure in the system at the time that the transfer device is disconnected from the first host device, the transfer device may open a valve to the pressure reservoir to introduce additional pressure into the breathing circuit at 214 in order to maintain the positive pressure on the patient's airway. As noted before, this can help to maintain the gain in the recruited lung volume achieved by previous lung volume recruitment procedures performed by the first host device.

At 216, the transfer device is connected to a second host device, the second host device includes a ventilator which will continue respiratory support to the patient. At 218 the inspiratory valve and expiratory valves are opened and at 220 respiratory support is delivered with the second host device to the patient through the transfer device.

In embodiments of the transfer device that include the memory, at 222 the stored ventilator settings, ventilation history, and/or patient data are uploaded from the memory of the transfer device to the second host device so that the ventilator conditions and settings at which respiratory support was previously provided, including the positive airway pressure applied to the patient are used at the outset of the delivery of respiratory support to the patient with the second host device. Similar to that as described above, as the second host device delivers respiratory support to the patient, the second host device stores ventilator settings, ventilation history and/or patient data at the memory of the transfer device that this information may be transferred to a subsequent host device, if needed.

In embodiments of the transfer device that include a pressure reservoir, the second host device operates in conjunction with the transfer device in order to pressurize the pressure reservoir at 226 with gas provided through the inspiratory port of the transfer device.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined, by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A patient transfer device for use with at least one host device comprising a ventilator capable of providing pressurized respiratory support to a patient, the patient transfer device comprising:
   an inspiratory port configured to pneumatically connect to the at least one host device to receive a flow of inspiratory gases;
   an inspiratory connection pneumatically connected to the inspiratory port;
   an expiratory port configured to pneumatically connect to the at least one host device;
   an expiratory connection pneumatically connected to the expiratory port;
   an inspiratory valve coupled between the inspiratory port and the inspiratory connection and operable between a first configuration that permits flow between the inspiratory port and the inspiratory connection and a second configuration that occludes flow between the inspiratory port and the inspiratory connection;
   an expiratory valve coupled between the expiratory port and the expiratory connection and operable between a first configuration that permits flow between the expiratory port and the expiratory connection and second configuration that occludes flow between the expiratory port and the expiratory connection;
an inspiratory tube connecting the inspiratory valve to the inspiratory connection;
an expiratory tube connecting the expiratory valve to the expiratory connection;
a recirculation tube extending between the inspiratory tube and the expiratory tube; and
at least one recirculation valve pneumatically connected to the recirculation tube, the recirculation valve operable to open when the inspiratory valve and expiratory valve are closed and operable to close when the inspiratory valve and expiratory valve are open;
wherein the inspiratory valve and the expiratory valve are configured to operate in the second configuration when the patient transfer device is disconnected from the at least one host device.

2. The patient transfer device of claim 1, further comprising a breathing circuit comprising:
a patient interface configured to pneumatically seal across an airway of a patient;
an inspiratory limb coupled between the inspiratory connection and the patient interface; and
an expiratory limb coupled between the expiratory connection and the patient interface;
wherein a closed pneumatic system is created within the breathing circuit when the inspiratory valve and the expiratory valve are closed.

3. The patient transfer device of claim 1, further comprising:
at least one registration feature extending from the patient transfer device, the at least one registration feature configured to engage a mated portion of the at least one host device.

4. The patient transfer device of claim 1, wherein the at least one recirculation valve is combined with at least one of the inspiratory valve and the expiratory valve.

5. The patient transfer device of claim 4, further comprising:
a processor communicatively connected to the at least one recirculation valve such that the processor operates the at least one recirculation valve to open and close.

6. The patient transfer device of claim 5, further comprising:
a pressure reservoir, the pressure reservoir configured to store pressurized gas;
a pressure valve that selectively pneumatically connects the pressure reservoir to the recirculation tube; and
at least one pressure transducer communicatively connected to the processor, wherein the processor monitors a pressure measured by the pressure transducer and selectively opens the pressure valve to maintain the pressure measured by the pressure transducer.

7. The patient transfer device of claim 1, further comprising:
a communication device configured to communicatively connect to the at least one host device;
a processor connected to the communication device; and
a memory, communicatively connected to the processor and operated by the processor to store data received at the communication device.

8. The patient transfer device of claim 7, wherein the data received at the communication device is received from the at least one host device and comprises at least one of a ventilator setting, a ventilation history, and patient data.

9. A respiratory support system comprising:
a first host device comprising a first ventilator and a first transfer bay, the first host device configured to provide a positive pressure for respiratory support to a patient;
a second host device comprising a second ventilator and a second transfer bay, the second host device configured to provide the positive pressure for respiratory support to the patient; and
a patient transfer device configured to be received within either of the first transfer bay and the second transfer bay, the patient transfer device comprising:
an inspiratory port configured to selectively pneumatically connect to the first or second host devices to receive flow of inspiratory gases from the first and second ventilators;
an inspiratory connection pneumatically connected to the inspiratory port;
an expiratory port configured to pneumatically connect to the at least one host device;
an expiratory connection pneumatically connected to the expiratory port;
an inspiratory valve coupled between the inspiratory port and the inspiratory connection operable between a first configuration that permits flow of pressurized gas from the inspiratory port to the inspiratory connection and a second configuration that occludes release of pressurized gas through the inspiratory port from the inspiratory connection;
an expiratory valve coupled between the expiratory port and the expiratory connection and operable between a first configuration that permits flow of pressurized gas from the expiratory connection to the expiratory port and a second configuration that occludes release of pressurized gas through the expiratory port from the expiratory connection, wherein the inspiratory valve and the expiratory valve operate in the second configurations when the patient transfer device is disconnected from the first and second host devices, to maintain the positive pressure when the patient transfer device is disconnected from the first and second host devices;
an inspiratory tube connecting the inspiratory valve to the inspiratory connection;
an expiratory tube connecting the expiratory valve to the expiratory connection;
a recirculation tube extending between the inspiratory tube and the expiratory tube; and
at least one recirculation valve pneumatically connected to the recirculation tube, the recirculation valve operable to open when the inspiratory valve and expiratory valve are closed and operable to close when the inspiratory valve and expiratory valve are open
a breathing circuit comprising a patient interface configured to pneumatically seal across an airway of a patient;
an inspiratory limb coupled between the inspiratory connection and the patient interface; and
an expiratory limb coupled between the expiratory connection and the patient interface.

10. The respiratory support system of claim 9, wherein the patient transfer device further comprises:
a processor;
a pressure reservoir, the pressure reservoir configured to store pressurized gas;

a pressure valve communicatively connected to the processor, the pressure valve operable to selectively pneumatically connect the pressure reservoir to the recirculation tube; and at least one pressure transducer communicatively connected to the processor, wherein the processor monitors a pressure measured by the pressure transducer and selectively opens the pressure valve to maintain the pressure measured by the pressure transducer.

11. The respiratory support system of claim 9, wherein the patient transfer device further comprises:
a communication device configured to communicatively connect to a first processor of the first host device and a second processor of the second host device;
a transfer device processor connected to the communication device; and
a memory, communicatively connected to the transfer device processor and operated by the transfer device processor to store data received at the communication device from the first host device, wherein the data comprises at least one of a ventilator setting, a ventilation history, and patient data.

12. The respiratory support system of claim 11, wherein the transfer device processor and the communication device communicatively connect to the second processor of the second host device and upload the data from the memory to the second host device.

13. A method of providing respiratory support to a patient, the method comprising:
delivering pressurized respiratory support to the patient with a first host device comprising a first ventilator through a transfer device, the transfer device receives a flow of inspiratory gases from the first host device through an inspiratory port and provides the inspiratory gases to the patient through a breathing circuit and expired gases from the patient are returned through the breathing circuit to the transfer device and to the first host device through an expiratory port of the transfer device;
closing an inspiratory valve associated with the inspiratory port and an expiratory valve associated with the expiratory port to create a closed pneumatic system between the breathing circuit and the transfer device;
disconnecting the transfer device from the first host device;
monitoring the pressure in the closed pneumatic system;
selectively opening a pressure reservoir to maintain the positive airway pressure within the closed pneumatic system;
reconnecting the transfer device to a second host device comprising a second ventilator;
opening the inspiratory valve and the expiratory valve; and
delivering respiratory support to the patient with the second host device through the transfer device, the transfer device receives a second flow of inspiratory gases from the second host device through the inspiratory port and provides the inspiratory gases to the patient through the breathing circuit and expired gases from the patient are returned through the breathing circuit to the transfer device and to the second host device through the expiratory port of the transfer device.

14. The method of claim 13, wherein the delivering of the respiratory support to the patient with the first host device further comprises providing a positive airway pressure to the patient and the delivering of respiratory support to the patient with the second host device further comprises continuing providing the positive airway pressure to the patient.

15. The method of claim 14, further maintaining the positive airway pressure within the closed pneumatic system while the inspiratory and expiratory valves are closed until the inspiratory and expiratory valves are opened.

16. The method of claim 13, further comprising:
operating the first host device and the transfer device in coordination to deliver the flow of inspiratory gases to the pressure reservoir to pressurize the pressure reservoir.

17. The method of claim 13, further comprising:
communicatively connecting a first processor associated with the first host device to a transfer device processor;
storing at least ventilator settings from the first ventilator on a memory of the transfer device;
communicatively connecting the transfer device processor to a second processor associated with the second host device;
uploading the at least ventilator settings from the first ventilator from the memory of the transfer device to the second ventilator; and
delivering respiratory support to the patient with the second host device according to the ventilator settings.

* * * * *